US012402878B2

(12) United States Patent
Wales et al.

(10) Patent No.: US 12,402,878 B2
(45) Date of Patent: Sep. 2, 2025

(54) SYSTEMS, DEVICES, AND RELATED METHODS FOR FASTENING TISSUE

(71) Applicant: Boston Scientific Scimed, Inc., Maple Grove, MN (US)

(72) Inventors: Ryan Wales, Northborough, MA (US); Jeff Gray, Sudbury, MA (US); Michael Peachock, Olmsted Falls, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/754,909

(22) PCT Filed: Oct. 20, 2020

(86) PCT No.: PCT/US2020/056472
§ 371 (c)(1),
(2) Date: Apr. 15, 2022

(87) PCT Pub. No.: WO2021/080976
PCT Pub. Date: Apr. 29, 2021

(65) Prior Publication Data
US 2024/0299027 A1 Sep. 12, 2024

Related U.S. Application Data

(60) Provisional application No. 62/924,557, filed on Oct. 22, 2019.

(51) Int. Cl.
*A61B 17/072* (2006.01)
(52) U.S. Cl.
CPC .. *A61B 17/072* (2013.01); *A61B 2017/07257* (2013.01); *A61B 2017/07271* (2013.01); *A61B 2017/07285* (2013.01)

(58) Field of Classification Search
CPC .................................. A61B 17/07207
See application file for complete search history.

(56) References Cited

U.S. PATENT DOCUMENTS 5,330,486 A * 7/1994 Wilk .................... A61B 17/115
227/181.1
5,833,695 A * 11/1998 Yoon ................ A61B 17/07207
227/176.1
(Continued)

FOREIGN PATENT DOCUMENTS

GB 927936 A 6/1963
KR 101209589 B1 12/2012
WO 9622055 A1 7/1996

OTHER PUBLICATIONS

International Search Report and Written Opinion issued in International Application No. PCT/US2020/056472 dated Jan. 22, 2021 (19 pages).

*Primary Examiner* — Nathaniel C Chukwurah
(74) *Attorney, Agent, or Firm* — Bookoff McAndrews PLLC

(57) ABSTRACT

A fastening device may comprise a flexible longitudinal body including a central longitudinal axis and a distal end; an anvil extending distally from the distal end of longitudinal body; and a distal body extending distally from the distal end of the longitudinal body. The distal body may be configured to removably receive a cartridge having a plurality of fasteners. At least one of the anvil and the distal body may be flexible and may have a first configuration with a distal portion of the at least one of the anvil and the distal body extending radially outward from the central longitudinal axis and a second configuration with the distal portion closer to the central longitudinal axis than in the first configuration.

16 Claims, 4 Drawing Sheets

(56) References Cited

U.S. PATENT DOCUMENTS

| | | | |
|---|---|---|---|
| 6,099,550 A * | 8/2000 | Yoon | A61B 10/06 |
| | | | 606/205 |
| 2005/0203547 A1 | 9/2005 | Weller et al. | |
| 2006/0151568 A1 | 7/2006 | Weller et al. | |
| 2007/0114261 A1 | 5/2007 | Ortiz et al. | |
| 2010/0114124 A1 | 5/2010 | Kelleher et al. | |
| 2013/0056520 A1 * | 3/2013 | Swensgard | A61B 17/07292 |
| | | | 227/177.1 |

* cited by examiner

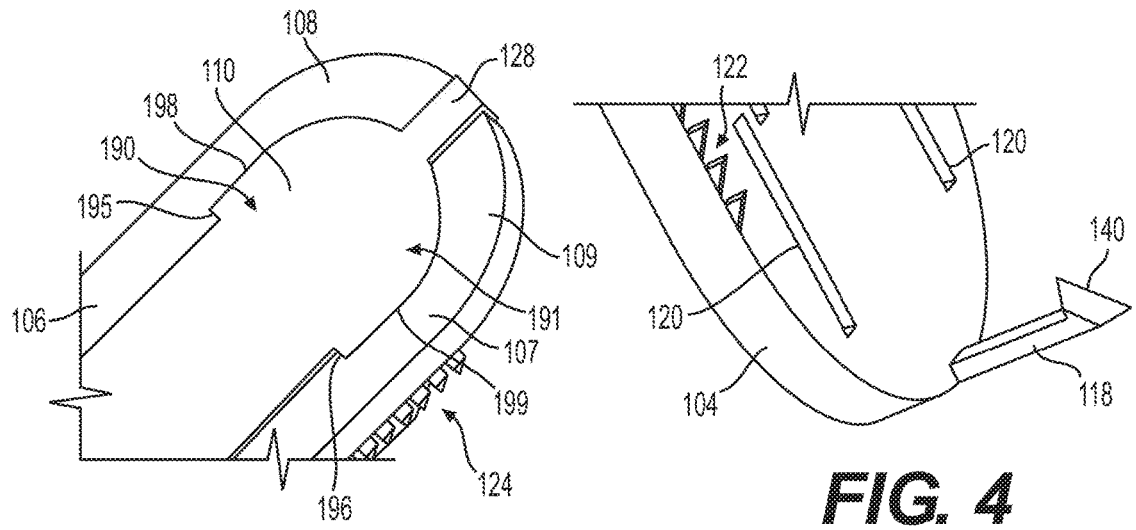
FIG. 3
FIG. 4
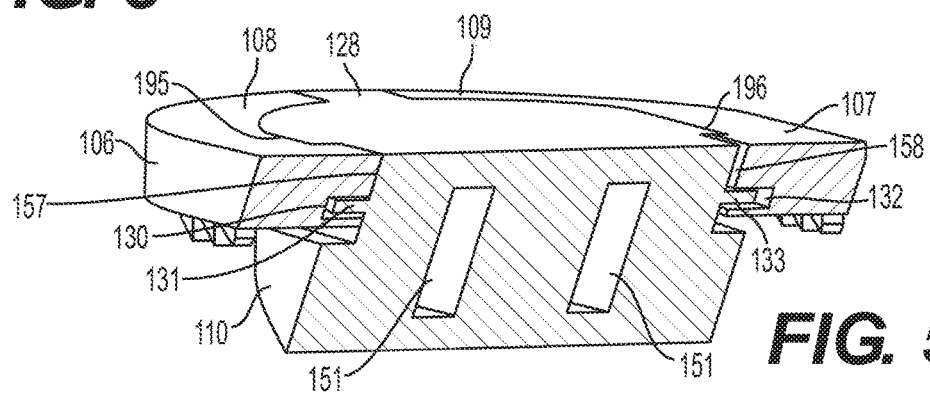
FIG. 5
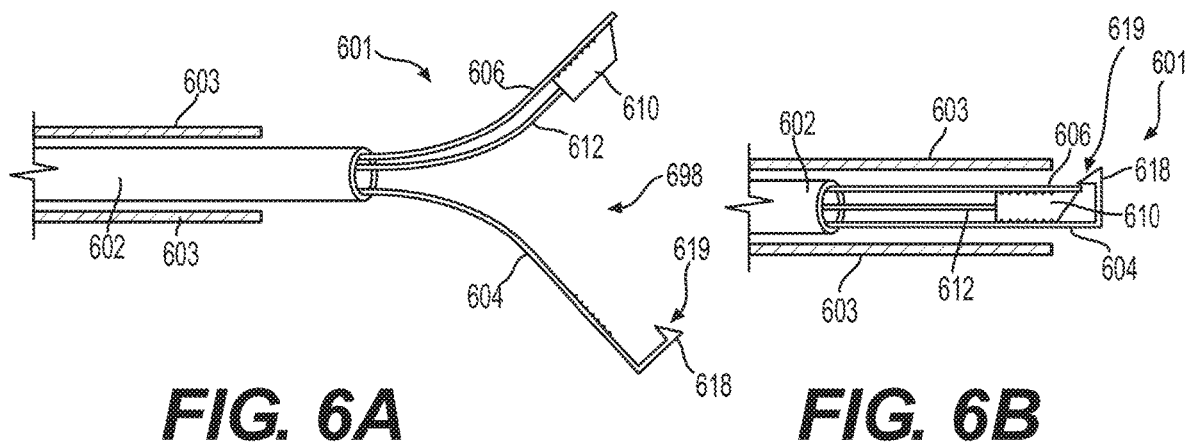
FIG. 6A
FIG. 6B

SYSTEMS, DEVICES, AND RELATED METHODS FOR FASTENING TISSUE

CROSS-REFERENCE TO RELATED APPLICATIONS

This application is a National Stage entry under 35 U.S.C. § 371 of International Application No. PCT/US2020/056472, filed Oct. 20, 2020, which claims the benefit of priority from U.S. Provisional Application No. 62/924,557, filed Oct. 22, 2019, each of which is incorporated by reference herein in its entirety.

TECHNICAL FIELD

Various aspects of the present disclosure relate generally to tissue fastening, including visualizing, retracting, and coupling tissue. More specifically, at least certain embodiments of the present disclosure relate to systems, devices, and related methods for stapling tissue, among other aspects.

BACKGROUND

Technological developments have given users of medical systems, devices, and methods, the ability to conduct increasingly complex procedures on subjects. The coupling of tissue in, for example, a subject's gastrointestinal tract, is a type of procedure in which difficulties may arise. One such difficulty involves replacing an empty staple cartridge with a new cartridge full of staples during a procedure. When a user deploys all of the fasteners stored in a cartridge of a surgical fastener, the user may need to remove the device from the patient's body, replace the cartridge with a cartridge full of fasteners, and re-insert the surgical fastener into the patient's body to continue fastening tissue. By removing and re-inserting the stapling device into the body of the patient, the user may cause damage to the body of the patient caused by the additional movement of the device through the patient's body required to replace the stapling cartridge. Also, the time of the procedure may be increased due to the processes of removing and re-inserting the stapling device in order to replace the cartridge of staples. There is a need for stapler instruments that address this difficulty.

SUMMARY

Aspects of the disclosure relate to, among other things, systems, devices, and methods for fastening tissue. Each of the aspects disclosed herein may include one or more of the features described in connection with any of the other disclosed aspects.

A fastening device may comprise a flexible longitudinal body including a central longitudinal axis and a distal end; an anvil extending distally from the distal end of longitudinal body; and a distal body extending distally from the distal end of the longitudinal body. The distal body may be configured to removably receive a cartridge having a plurality of fasteners. At least one of the anvil and the distal body may be flexible and may have a first configuration with a distal portion of the at least one of the anvil and the distal body extending radially outward from the central longitudinal axis and a second configuration with the distal portion closer to the central longitudinal axis than in the first configuration.

Any of the devices disclosed herein may have any of the following features. The fastening device may include a protrusion extending from a surface of anvil, and the protrusion may be configured to engage a distal body. The at least one of the anvil and the distal body may be the anvil; and the distal body may be flexible and have a first configuration with a distal portion of the distal body extending radially outward from the central longitudinal axis and a second configuration with the distal portion of the distal body closer to the central longitudinal axis than in the first configuration. Each of the distal body and the anvil may be curved in the respective first configuration and substantially straight in the second configuration. The cartridge may be removably coupled to the distal body. The distal body may include a groove configured to slidably receive a flange of the cartridge. The cartridge may include an actuation wire extending proximally from a proximal end of the cartridge through a channel of the longitudinal body, and the actuation wire may be configured to move proximally relative to the cartridge and the anvil to deploy fasteners from the cartridge. A distal portion of the cartridge may include a locking portion configured to be received by a locking gap of the distal body. The distal body may include a first distal body and a second distal body spaced from the first distal body. The cartridge may include a distal protrusion extending distally from a distal surface of the cartridge, and the distal protrusion may be configured to be received between distal ends of the first distal body and the second distal body. The distal body may include a first distal body and a second distal body separated by a gap configured to receive the cartridge. The device may further include a flexible catheter configured to translate relative to the longitudinal body, and the flexible catheter may move one or more of the anvil and the distal body towards each other when the flexible catheter is moved distally relative to the longitudinal body. The device may further include an I-beam including a top portion, a bottom portion, a distal-facing sharp edge and at least one actuation ramp, and the cartridge. The cartridge may be configured to receive the at least one actuation ramp. The I-beam may move proximally and distally relative to the anvil and the distal body. The distal-facing sharp edge may be proximal to a distal end of the I-beam and may extend between the top portion and the bottom portion of the I-beam. The device may further include a cartridge configured to hold a plurality of fasteners and including a proximal elongate extending proximally from a proximal end of the cartridge. The proximal elongate may include a lumen and at least one actuation wire positioned within the lumen. The actuation wire may be configured to deploy fasteners from the cartridge and/or actuate a knife within the cartridge. Each of the distal body and the anvil may include a radially-inward facing surface having at least one of a roughened surface, serrations, and teeth.

In another example, a tissue fastening device may comprise a flexible tube and a fastener device positioned within a lumen of the flexible tube. The fastener device may comprise a flexible anvil that has a first configuration with a distal portion of the anvil extending radially outward from the central longitudinal axis of the fastener device and a second configuration with the distal portion of the anvil closer to the central longitudinal axis of the fastener device than in the first configuration. The fastener device may also comprise a flexible distal body configured to removably receive a cartridge of fasteners. The flexible distal body may have a first configuration with a distal portion of the flexible distal body extending radially outward from the central longitudinal axis of the fastener device and a second configuration with the distal portion closer to the central longitudinal axis of the fastener device than in the first configuration. The tube may be configured to translate distally relative to the fastener device to transition each of the anvil and the flexible distal body from the respective first configuration to the respective second configuration.

Any of the devices disclosed herein may have any of the following features. The anvil may include a protrusion extending from a surface of the anvil. The protrusion may be configured to engage the flexible distal body. The cartridge may be removably coupled to the flexible distal body.

A medical method may comprise inserting a flexible fastening device into a flexible tube. The fastening device may include an anvil, at least one distal body, and a cartridge removably coupled to the distal body and holding a plurality of fasteners. The method may also comprise inserting the tube into a natural orifice of a body. The method may further comprise moving the tube distally relative to the fastening device such that the tube moves at least one of the anvil and the distal body from a first configuration with a distal portion of the at least one of the anvil and the distal body extending radially outward from a central longitudinal axis of the fastening device to a second configuration with the distal portion closer to the central longitudinal axis of the fastening device than in the first configuration. The method may also comprise deploying at least one fastener from the cartridge.

Any of the methods disclosed herein may include any of the following steps or features. The cartridge may be a first cartridge, and the method may further comprise uncoupling the first cartridge from the distal body, while the fastening device is in the body; removing the first cartridge from the body by moving the first cartridge proximally; and coupling a second cartridge to the distal body; wherein the second cartridge holds a plurality of fasteners.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 3 is a perspective view of a portion of an exemplary medical device, according to aspects of this disclosure.

FIG. 4 is a perspective view of a portion of an exemplary medical device, according to aspects of this disclosure.

FIG. 5 is a perspective view of a portion of an exemplary medical device with part of the medical device shown in cross-section, according to aspects of the present disclosure.

FIGS. 6A and 6B are side views of an exemplary surgical stapler system, according to aspects of this disclosure.

DETAILED DESCRIPTION

The present disclosure is drawn to systems, devices, and methods for coupling, cutting, and resecting tissue, among other aspects. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. The term "coupling tissue together" may refer, for example, to stapling, fixing, attaching, fastening, or otherwise joining two portions of tissue together. The term "fastener" may include staples, clips, elastic bands, suture, or any other fastener known in the art. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

Embodiments of the present disclosure may be used to visualize, cut, resect, and/or couple together target tissue in an endo-luminal space, or facilitate the process thereof. In particular, some embodiments combine a tissue resecting device with a tissue stapling device. The tissue stapling apparatus may include a resection or cutting mechanism (e.g., an integrated knife or sharp edge) and a stapling mechanism (stapler). The stapling apparatus may be delivered to target tissue through an endoscope working channel to the target tissue site. In some examples, the stapling apparatus may be back-fed through an endoscope, gastroscope, colonoscope, flexible catheter, or other medical device working channel prior to inserting the device into the body of the patient. The overall system may include a retraction mechanism, such as a tissue clip, to pull tissue towards the tissue stapling device. All or parts of the tissue stapling device and the retraction mechanism could be metallic, composite, plastic, or include a shape memory metal (such as nitinol), a shape memory polymer, a polymer, or any combination of materials.

Figure 1:
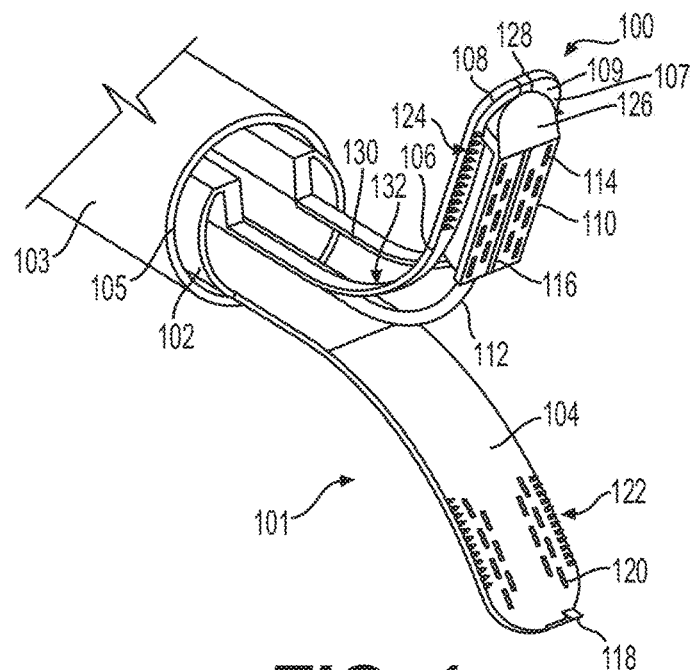
FIG. 1 is a perspective view of an exemplary surgical stapler system, according to aspects of this disclosure.

FIG. 1 shows a distal end of an exemplary surgical system 100 in accordance with an embodiment of this disclosure. System 100 may include a surgical stapling apparatus 101 configured to engage body tissue, apply a plurality of surgical fasteners thereto, and form an incision in the fastened body tissue. Surgical stapling apparatus 101 may be used during minimally invasive surgical procedures, such as laparoscopic or endoscopic procedures, or any other suitable medical procedure. Apparatus 101 may be used to apply surgical clips or other fasteners, but will be primarily discussed in the context of applying staples from a staple cartridge. Apparatus 101 is shown positioned within a flexible catheter 103 including a working channel 105 in which an elongate body 102 of apparatus 101 is positioned.

Figure 2A:
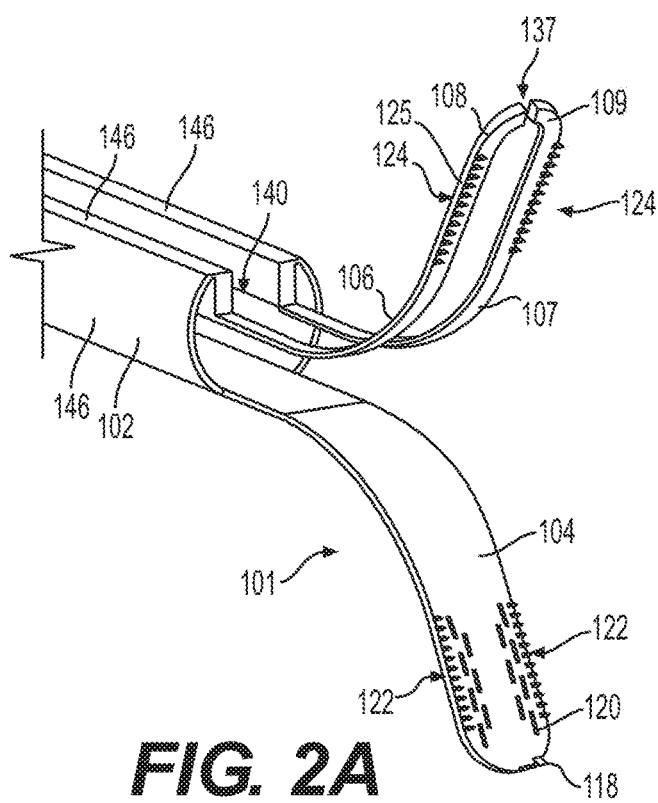
FIGS. 2A and 2B are perspective and side views, respectively, of an exemplary medical device according to aspects of this disclosure.
Figure 2B:
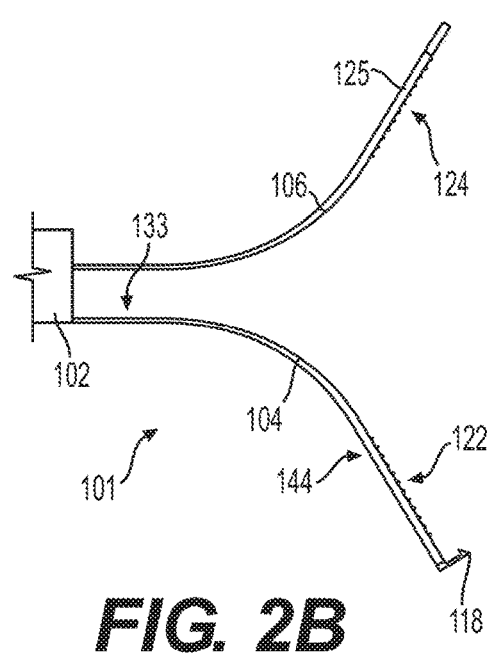

As illustrated in FIG. 1, elongate body 102 of apparatus 101 may be at least partially cylindrical, flexible, and configured to move through a working channel 105 of a medical device, such as catheter 103. Elongate body 102 may extend longitudinally from a proximal end (not shown) to a distal end (shown in FIG. 1). An anvil 104 and two distal bodies 106, 107 may extend distally from a distal portion of elongate body 102. Anvil 104 and distal bodies 106, 107 may extend from opposing portions of elongate body 102 and, in one configuration of bodies 106, 107, may curve or be biased radially outward in opposite directions from the longitudinal axis of elongate body 102 in a first, e.g., unconstrained or open, configuration. When catheter 103 slides distally over body 102, distal bodies 106, 107 and anvil 104 may move radially inward towards the central longitudinal axis of apparatus 101. In some examples, when catheter 103 slides distally over body 102, distal bodies 106, 107 may be moved towards anvil 104 and transition from the first configuration to a second, e.g., constrained or closed, configuration. In some examples, a user may position target tissue between anvil 104 and distal bodies 106, 107 so that when catheter 103 slides distally over body 102, anvil 104 and distal bodies 106, 107 clamp down onto the target tissue. When positioned in the second, e.g. constrained or closed configuration, teeth 122 of apparatus 101 may engage target tissue. A channel 140 (shown in FIG. 2) may extend longitudinally within a radially-outer surface of elongate body 102. At least proximal portions of radially-inward facing surfaces, relative to the longitudinal axis of elongate body 102, of each of anvil 104 and distal bodies 106, 107 may face each other. Anvil 104 and distal bodies 106, 107 may be flexible and at least distal portions thereof may be biased radially-outward from the longitudinal axis of elongate body 102. Such portions of anvil 104 and distal bodies 106, 107 may be configured to flex inward towards the central longitudinal axis of elongate body 102 such that anvil 104 and distal bodies 106, 107 are closer to or the same distance from the central longitudinal axis of elongate body as the radially-inner surface of elongate body 102. Anvil 104 and distal bodies 106, 107 may be spring steel, shape memory alloy, or any other material capable of being springing back or otherwise returning to its original shape after bending. In some examples, elongate body 102 may be coupled to an actuation wire, cable, or tube (not shown) at a proximal portion of elongate body 102, and movement of the actuation wire, cable, or tube proximally or distally may move elongate body 102 proximally or distally.

Anvil 104 may be configured to align with distal bodies 106, 107 when distal bodies 106, 107 are moved towards anvil 104. Anvil 104 may include a textured portion, such as teeth or serrations 122, at a distal portion of anvil 104. In some examples, anvil 104 may include recesses 120 and a protruding portion 118 at a distal end of anvil 104. Teeth or serrations 122 of anvil 104 may align with a textured portion, such as teeth or serrations 124, of distal portions 106, 107 when anvil 104 and distal portions 106, 107 are positioned substantially parallel to a longitudinal axis of elongate body 102. Anvil 104 has substantially flat upper and lower surfaces, a rounded or curved distal tip portion, and a proximal portion extending from a distal edge of elongate body 102. Recesses 120 of anvil 104 may be configured to received fasteners, such as staples. Recesses 120 may be configured to align with openings 114 of cartridge 110. Protruding portion 118 may extend radially-inward relative to the central longitudinal axis of elongate body 102 from the rounded distal tip portion of anvil 104. Protruding portion 118 may be hook-shaped and may be configured to engage cartridge 110. As shown in FIG. 4, protruding portion 118 may include an edge portion 140 terminating at a sharp point at an end of protruding portion 118. Edge portion 140 may be configured to pierce tissue so that protruding portion 118 may extend through tissue to engage or couple to at least one of distal bodies 106, 107 and cartridge 110 to hold apparatus 101 in a locked or clamped position, which may facilitate deployment of fasteners. A radially-outer surface 144 of anvil 104 may be configured and positioned to engage a surface of catheter 103, such as a surface defining lumen 105.

Distal bodies 106, 107 may have longitudinal axes parallel to each other and may curve towards each other at their distal ends 108, 109. In some examples, distal ends 108, 109 may be spaced from each other to provide a gap to receive a distal protrusion 128 of a stapler cartridge 110 (shown in FIG. 3). Each distal body 106, 107 may include textured protrusions, such as a serrated or teeth portions 124 positioned at a distal portion of distal bodies 106, 107. Serrated or teeth portions 124 may be configured to grip tissue and may be positioned at or proximate to an outer edge 125 (shown in FIG. 2) of distal bodies 106, 107. Each distal body 106, 107 may be spaced from the radially outermost surfaces 146 of elongate body 102. Radially-outer surfaces of distal bodies 106, 107 may be configured and positioned to engage a surface of a working channel of a medical device, such as a surface defining lumen 105 in catheter 103. Anvil 104 may extend from a distal edge of elongate body 102 and a proximal space 133 between distal bodies 106, 107 and anvil 104 may be less than the diameter or cross-sectional dimension of elongate body 102.

Any of the embodiments disclosed herein may have only one of anvil 104 or distal bodies 106, 107 that curves radially outward, is flexible, and transitions between a configuration spaced from the longitudinal axis of elongate body 102 (to accept tissue) to a stapling configuration that may be substantially parallel to the axis. The other (anvil 104 or distal bodies 106, 107) may extend substantially parallel to the longitudinal axis of elongate body 102, may be straight and/or substantially inflexible, and may not transition between spaced and stapling configurations.

Distal bodies 106, 107 may be configured to hold a fastener cartridge 110, as shown in FIG. 1. FIG. 5 shows a perspective view of distal bodies 106, 107 with a stapler cartridge 110 positioned within grooves 130, 132 of distal bodies 106, 107, with portions of distal bodies 106, 107 and cartridge 110 shown in a cross-section. Each groove 130, 132 of distal bodies 106, 107 may extend from distal ends 108, 109 to a proximal portion of elongate body 102. Groove 130 of distal body 106 may be positioned on a first surface 157 opposing a second surface 158 of distal body 107 in which groove 132 is positioned. In some examples, grooves 130, 132 may extend to the proximalmost end of elongate body 102. Grooves 130, 132 may be configured to slidably receive protrusions or tangs 131, 133 respectively of stapler cartridge 110.

In some examples, distal bodies 106, 107 may include a locking gap portion 190 between a distal portion of each distal body 106, 107. Opposing surfaces 198, 199 surrounding locking gap portion 190 of distal bodies 106, 107 may be spaced farther apart than opposing surfaces, such as first surface 157 and second surface 158, at a proximal portion of distal bodies 106, 107, and ledges 195, 196 may be formed on distal bodies 106, 107. Ledges 195, 196 may be configured to receive a locking portion 191 of cartridge 110. In some examples, grooves 130, 132 may end at ledges 195, 196 (e.g. extending from a proximal end to ledges 195, 196). A further discussion of how locking gap portion 190 may prevent movement of cartridge 110 and may facilitate positioning of cartridge 110 is described below. In some examples, distal bodies 106, 107 may not include locking gap portion 190.

Cartridge 110 may be configured to be positioned between distal bodies 106, 107. Cartridge 110 may include openings 114 configured to deploy fasteners and a longitudinal slot 116 configured to receive a cutting device, such as a knife. A distal portion 126 of cartridge 110 may be angled relative to the longitudinal axis of cartridge 110. Cartridge 110 may also include tangs 131, 133 extending transverse to a longitudinal axis of cartridge 110. Tangs 131, 133 may be sized to be received within grooves 130, 132. In some examples, tangs 131, 133 may be sized to fit within grooves 130, 132 and allow sliding movement of cartridge 110 in the proximal-distal directions and slight side-to-side and/or up-to-down movement in a direction transverse to the proximal-distal directions. In some embodiments, the tangs 131, 133 and/or the grooves 130, 132 may include a taper, so that the tangs 131, 133 may form a secure fit in the grooves 130, 132 when positioned in the distal bodies 106, 107. For example, pushing the cartridge 110 distally relative to the distal bodies 106, 107, may engage and secure the cartridge 110 in a desired position. When the cartridge 110 should be removed and/or replaced, the cartridge can be manipulated by pulling proximally relative to the distal bodies 106, 107 to disengage the tapered portions of the tangs 131, 133 and/or the grooves 130, 132. In addition, cartridge 110 may include one or more cavities 150, 151 (shown in FIG. 5). Cavities 150, 151 may be configured to receive one or more actuators, one or more fasteners, one or more pistons or spacers, and/or one or more knives. A proximal elongate 112 may extend from a proximal portion of cartridge 110. Proximal elongate 112 may be cylindrical and may include a lumen (not shown) for receiving one or more actuation wires for deploying fasteners and/or for moving one or more cutting devices (such as a knife). Proximal elongate 112 may be flexible and may be configured to move through elongate body 102. Proximal elongate 112 may be sufficiently rigid to translate cartridge 110 distally when a user moves a proximal portion of proximal elongate 112 distally. In some examples, proximal end of proximal elongate 112 may include a spool style handle, a wheel shaped knob, and/or any other suitable activation mechanism known in the art, that deploys fasteners by either pulling or rotating. Cartridge 110 may include a distal protrusion 128, and distal protrusion 128 may be configured to be positioned within gap 137 between distal portions 108, 109 of distal bodies 106, 107.

FIGS. 6A and 6B are side views of an exemplary surgical stapling apparatus 601 substantially similar to apparatus 101. Any of the features discussed with regard to apparatus 101 may be included in apparatus 601. Apparatus 601 is shown positioned within flexible catheter 603 (shown in cross-section). Apparatus 601 includes distal body 606, anvil 604 including protruding portion 618, staple cartridge 610, elongate body 602, and proximal elongate 612. Apparatus 601 may also include a second distal body, like distal body 107, but not shown in the views of FIGS. 6A-6B. In FIG. 6A, apparatus 601 is positioned with anvil 604 and distal body 606 separated in an expanded, open configuration. In some examples, apparatus 601 may be back-fed into flexible catheter 603, which may include moving the proximal end (not shown) of apparatus 601 through distal opening 601 of flexible catheter 603 in order to position anvil 604 and distal body 606 proximate to distal opening 601. A user may first position tissue within space 698 (the active region of apparatus 601) between anvil 604 and distal body 606. The user may then move flexible catheter 603 distally relative to apparatus 601 and cause curved outer surface portions of anvil 604 and distal body 606 to contact inner surfaces of flexible catheter 603. By moving flexible catheter 603 distally relative to apparatus 601, anvil 604 and distal body 606 may be moved towards each other to clamp tissue between anvil 604 and distal body 606. In other embodiments, as discussed above, one of anvil 604 or distal body 606 may be substantially straight, may be substantially inflexible, may extend substantially parallel to the longitudinal axis of elongate body 602, and may remain in the same position as flexible catheter 603 is moved distally, thus causing only the other of anvil 604 or distal body 606 to move radially inward as flexible catheter 603 is moved distally.

In some examples, protruding portion 618 of anvil 604 may assist in holding anvil 604 and distal body 606 in a closed configuration (clamped together) to allow a user to deploy staples or other fasteners. For example, protruding portion 618 may include a flange 619, and flange 619 may engage cartridge 610 and/or an outer surface of distal body 606, to hold distal body 606 (shown in FIG. 6B) in a clamped position and prevent distal body 606 from moving radially-outward relative to the longitudinal axis of body 602. By holding anvil 604 and distal body 606 clamped together, protruding portion 618 may allow the user to stop moving flexible catheter 603 distally, moving apparatus 601 proximally, and/or applying a force in the distal direction to catheter 603 (in order to hold anvil 604 and distal body 606 together) since anvil 604 and distal body 606 will be held in a closed, clamped position. The user may then proceed to deploy staples from cartridge 610. In some examples, the user may pull an actuator, which may be positioned within proximal elongate 612, to deploy staples from cartridge 610 when anvil 604 and distal body 606 are clamped together (shown in FIG. 6B). An example of such activation will be described herein with respect to FIG. 7. To release protruding portion 618 from cartridge 610, the user may move flexible catheter 603 distally to contact flange 619 and move flange 619 distally to release cartridge 610 from contacting flange 619. Since distal body 606 may be biased towards an open position shown in FIG. 6A, when flange 619 is moved distally out of contact with cartridge 610, distal body 606 will move radially outward and away from anvil 604. Alternatively, the user may pull the staple cartridge 610 proximally to move flange 619 out of contact with the staple cartridge 610. In some examples, anvil 604 may not include a protruding portion 618, and the user may hold anvil 604 and distal body 606 in a closed, clamped position by holding flexible catheter 603 in a position that forces anvil 604 and distal body 606 in a clamped position. While apparatus 601 is shown positioned within flexible catheter 603, apparatus 601 may operate in the same manner as described above when positioned within a working channel of another type of medical device, such as a working channel of an endoscope, gastroscope, colonoscope, ureteroscope, or the like.

Figure 7:
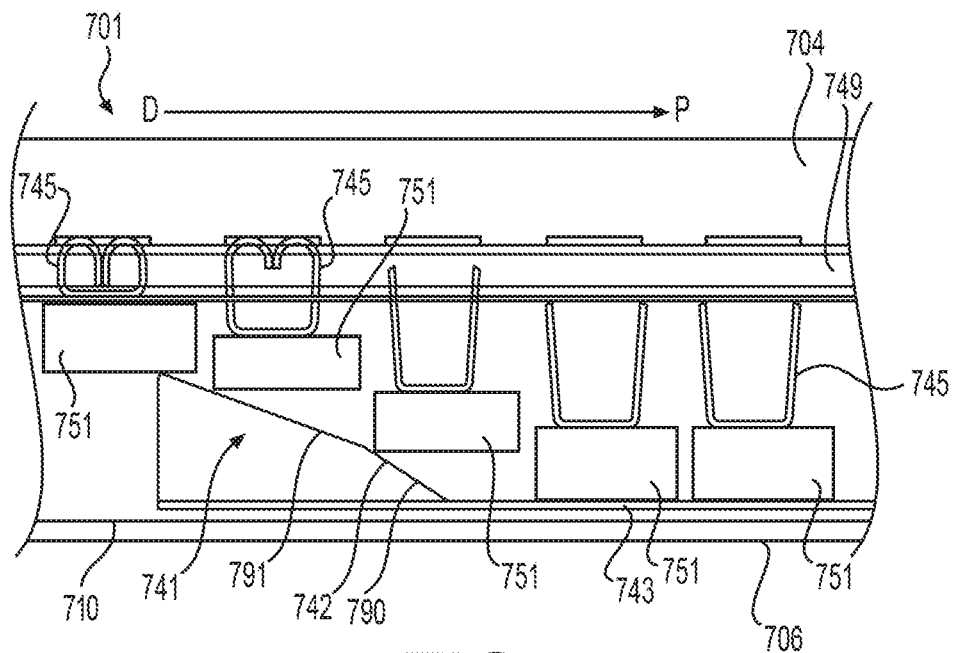
FIG. 7 is a side view of a portion of an exemplary surgical stapler system, according to aspects of the present disclosure.

FIG. 7 shows an enlarged, cross-sectional view of an exemplary stapling apparatus 701 including anvil 704, distal body 706, cartridge 710 with fasteners 745 (staples), and an actuation sled 741 with actuation body 743. Any of the components of apparatus 701 may include any of the features discussed herein regarding the components of other stapling apparatuses 101, 601. The components shown within cartridge 710 may be positioned with cavity 150, cavity 151, a single cavity within a cartridge, or a plurality of cavities within a cartridge. The apparatus 701 in FIG. 7 is shown deploying fasteners 745 onto tissue 749. Actuation sled 741 engages pistons or spacers 751, and the pistons or spacers 751 then engage the fasteners 745 to deploy the fasteners 745. As shown in FIG. 7, actuation sled 741 engages the pistons or spacers 751 as actuation sled 741 moves in the proximal direction P. Each piston or spacer 751 may be configured to translate within cartridge 710 and may be sized to engage only one fastener 345. In other examples, each piston or spacer 751 may be sized to engage multiple fasteners 345, or one or more pistons or spacers 751 may be sized to engage multiple fasteners 345 while one or more other pistons or spacers 751 may be sized to engage only one fastener 345. Actuation sled 741 may be configured to move each piston or spacer 751 in a direction transverse to the longitudinal axis of distal body 706.

For example, actuation sled 741 and actuation body 743 (which may be a wire or cable, extending to a proximal handle) may be pulled proximally, which may move ramp 742 (including first portion 790 and second portion 791) into contact with one or more pistons or spacers 751 and push one or more pistons or spacers 751 to deploy one or more fasteners 745 from cartridge 710. First portion 790 of ramp 742 may have a steeper incline relative to second portion 791. Each of the pistons or spacers 751 may have an upper surface that aligns and/or is flush with a portion of each respective fastener 745. For example, each fastener 745 may be a staple and may include three substantially flat sections (e.g., a "U-shape") with the middle substantially flat section aligning with the top surface of each spacer 751. Each piston or spacer 751 may be sufficiently rigid to move uniformly upward when the ramp 742 of actuation sled engages a corner of the piston or spacer 751. In some examples, each piston or spacer 751 may be coupled to cartridge 710 such that movement along the longitudinal axis of cartridge 710, or in the proximal P or distal D directions shown in FIG. 7, is prevented while allowing movement in a direction perpendicular to the longitudinal axis of cartridge 710. The pistons or spacers 751 in cartridge 710 may prevent fasteners 745, such as staples, from partially deploying and may avoid improper stapling caused by a distal portion of a staple moving upward when a proximal portion of the staple does not move. By providing spacers 751 with flat top surfaces that align with fasteners 745, the ramp 742 of actuation sled 741 can move proximally and push each fastener 745 uniformly upward by engaging each spacer 751. When fasteners 745 are deployed from cartridge 710, fasteners 745 may engage recesses 760 of anvil 704 (for example) to facilitate fastening to tissue 749.

After the user has deployed all of the fasteners 745 from cartridge 710, the user may then remove cartridge 710 from distal body 706 and replace cartridge 710 with a new cartridge full of fasteners. For examples, referring to FIGS. 1 and 5, the user may move cartridge 110 proximally by pulling proximal elongate 112 proximally, and cartridge 110 may slide proximally through elongate body 102 within grooves 130, 132 and be removed by the user at a proximal portion of elongate body 102. Once completely removed from apparatus 101, the user may replace cartridge 110 with a new cartridge full of fasteners. The user may then position the new cartridge within grooves 130, 132 and move the new cartridge distally to distal bodies 106, 107. Once the new cartridge is positioned at the distal end of distal bodies 106, 107, the user may continue fastening tissue using the new cartridge. By providing a way to remove and replace staple cartridges without having to remove the entire stapling apparatus 101 from a working channel, the user may avoid or minimize unnecessary damage to the patient caused by the removal and re-insertion of apparatus 101 out of and into the patient's body during a procedure. Also, replacing an empty staple cartridge with a new cartridge without having to remove the entire stapling apparatus 101 from the patient's body may reduce procedure time.

In some examples, any of the cartridges 110, 610, 710 discussed herein may include a locking portion 191. Locking portion 191 may be configured to be received by a locking gap portion 190 between distal bodies 106, 107. Locking portion 191 may be positioned between distal bodies 108, 109 and tangs 131, 133 may be positioned within grooves 130, 132 of distal bodies 106, 107. An outer portion of locking portion 190 that is radially-outermost from the central longitudinal axis of cartridge 110 may be positioned adjacent to and slidably engaged with distal bodies 106, 107 as cartridge is moved from a proximal portion of distal bodies 106, 107 to locking gap portion 190. For example, cartridge 110 may be moved distally or proximally with tangs 131, 133 positioned within grooves 130, 132 while locking portion 191 is positioned adjacent to distal bodies 106, 107. When cartridge 110 is positioned such that locking portion 191 is distal to ledges 195, 196 of distal bodies 106, 107, locking portion 191 may be moved upward (or away from anvil 104) to a position between distal bodies 106 107 within locking gap portion 190. Once locking portion 191 is positioned within locking gap portion 190, ledges 195, 196 may prevent cartridge 110 from moving proximally, and distal portions 108, 109 of distal bodies 106, 107 may prevent cartridge 110 from moving distally. In some examples, distal protrusion 128 may provide a visual notification to the user when locking portion 191 is properly positioned within locking gap portion 190 because the user may identify when distal protrusion 128 is positioned within gap 137, for example via an image sensor such as image sensor 864 described herein. When the user could like to remove cartridge 110 from locking gap portion 191, the user may move cartridge 110 in a direction transverse to the longitudinal axis of distal bodies 106, 107 until locking portion 191 is not in contact with ledges 195 196, and then move cartridge 110 proximally.

In some examples, cartridge 110 may be moved distally or proximally with tangs 131, 133 of locking portion 191 positioned within grooves 130, 132 such that distal bodies 106, 107 are moved radially outward due to locking portion 191 being positioned between distal bodies 106, 107. Grooves 130, 132 may extend to the distal ends of distal bodies 106, 107. When cartridge 110 is positioned such that locking portion 191 is distal to ledges 195, 196 of distal bodies 106, 107, distal bodies 106, 107 may move radially inward towards locking portion 191 to a position distal bodies 106 107 abutting locking portion 191 within locking gap portion 190. Once locking portion 191 is positioned within locking gap portion 190, ledges 195, 196 may prevent cartridge 110 from moving proximally, and distal portions 108, 109 of distal bodies 106, 107 may prevent cartridge 110 from moving distally.

Figure 8:
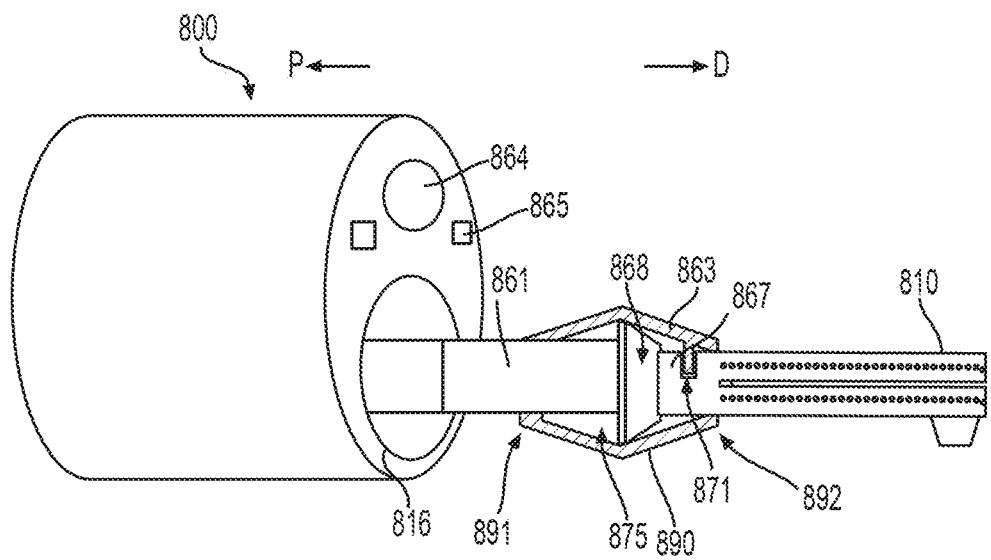
FIG. 8 is a side view of exemplary surgical stapler system, according to aspects of this disclosure.

FIG. 8 shows an embodiment of a cartridge 810 and a proximal elongate member 861 extending out of a working channel 816 of distal tip 800 of a medical device, such as an endoscope or any other device mentioned herein. Distal tip 800 may include one or more image sensors 864 and one or more illuminators 865. Cartridge 810 may be configured to operate with embodiments of stapler apparatuses similar to apparatus 101 or 601 that do not require the stapling actuator, such as actuation sled 741, to be part of the cartridge 810, such as stapling apparatus 901 discussed herein below. Cartridge 810 may include a coupling protrusion 867 configured to mate with coupler 863. Surfaces of cartridge 810 may include cuts, slots, ridges, or other features that add flexibility to cartridge 810, permitting cartridge 810 to more easily extend through working channel 816. Similarly, proximal elongate member 861 may be flexible yet sufficiently rigid to move cartridge 810 through working channel 816. Cartridge 810 may be coupled to proximal elongate member 861 via coupler 863. In some examples, elongate member 861 may be configured to be back-fed through an endoscope working channel or other medical device prior to coupling cartridge 810 to elongate member 861.

Coupler 863 is shown in cross-section in FIG. 8. In some examples, coupler 863 may mate with cartridge 810 and may be releasable via an actuator. In some examples, coupler 863 may be releasable without an actuator. The proximal end of elongate member 861 may have at least one user interface to release coupler 863 from cartridge 810. Coupler 863 may be cylindrical, may cover portions of each of proximal elongate member 861 and cartridge 810, and may include a lumen 875 extending through the central longitudinal axis of coupler 863. In some examples, coupler 863 may include a radially-outer surface 890 that extends towards the central longitudinal axis of coupler 863 as the radially-outer surface moves from a longitudinal midpoint towards proximal end 891 and distal end 892 of coupler 863. In some examples, a chamfered tip 868 of elongate member 861 may be configured to be received by coupler 863 to couple cartridge 810 to elongate member 861. Chamfered tip 868 may be rigid and may be positioned within lumen 875 of coupler 863 (shown in FIG. 8). Coupler 863 may be flush and/or in contact with the exterior surface of elongate member 861 at a portion proximal to the chamfered tip 868. Chamfered tip 868 may facilitate breaking coupler 863 to release cartridge 810 from elongate member 861. For example, a user may pull elongate member 861 proximally to pull coupler 863 proximally such that an exterior surface of coupler 863 contacts distal tip 800, for example coupler 863 may contact a distal front face of distal tip 800 proximate to an edge portion of working channel 816. When coupler 863 comes into contact with distal tip 800, chamfered tip 868 may be pulled proximally such that chamfered tip 868 applies pressure against an interior surface of coupler 863, which may compress coupler 863 via chamfered tip 868 moving proximally and coupler 863 abutting distal tip 800. Compressing coupler 863 between distal tip 800 and chamfered tip 868 may cause coupler 863 to break and release cartridge 810 from coupler 863. In some examples, coupler 863 may break into several pieces and be released into a body of a patient during a procedure. In some examples, coupler 863 may be cylindrical and may include an interior portion configured to receive proximal elongate member 861 and cartridge 810. Coupler 863 may be overmolded and/or contain an overmolded feature in the shape of cartridge 810. In some examples, an overmolded feature of coupler 863 may be overmolded over cartridge 810 such that once cartridge 810 is closed onto tissue to deploy staples from cartridge 810, the tension applied to the entire assembly by the operator, due to stapling tissue using cartridge 810, exceeds the material strength of coupler 863 and breaks coupler 863, which may then release cartridge 810. In some examples, coupler 863 may be biodegradable and/or digestible, and may be configured to break off from elongate member 861 and left within the body of a patient. In some examples, cartridge 810 may be manufactured with a portion of coupler 863 positioned within recess 871 of cartridge 810. A user may use coupler 863 and proximal elongate 861 to deliver cartridge 810 to a stapling apparatus, such as stapling apparatus 901, couple cartridge 810 to stapling apparatus 901, and release cartridge 810 from coupler 863. In some examples, coupler 863 may be configured to break off from cartridge 810 after cartridge is fastened to or clamped down on tissue. In some examples, elongate member 861 and coupler 863 may be used to retrieve an empty staple cartridge from an apparatus, such as apparatus 901. Cartridge 810 may include teeth on a surface of cartridge 810 configured to mate with one or more distal bodies, such as distal bodies 906, 907, to facilitate coupling cartridge 810 to the one or more distal bodies.

In some examples, a user may deliver cartridge 810 to a distal portion of distal bodies 906, 907 (shown in FIG. 9) using proximal elongate 861 and coupler 863. A user may move proximal elongate 861 to coupler cartridge 810 to distal bodies 907, 908, which in some examples may be a snap-fit. Once cartridge 810 is fixedly coupled to distal bodies 907, 908, the user may pull proximal elongate 861 proximally. When pulling proximal elongate 861 proximally, chamfered tip 868 may apply pressure against the interior surface of coupler 863 because cartridge 810 is preventing coupler 863 from moving proximally with proximal elongate 861. In some examples, the pressure created from the user pulling proximal elongate 861 proximally and chamfered tip 868 contacting the interior surface of coupler 863 may cause coupler 863 to break and release cartridge 810 from coupler 863. In some examples, cartridge 810 may remain fixedly coupled to distal bodies 907, 908 after coupler 863 releases from cartridge 810.

Figure 9:
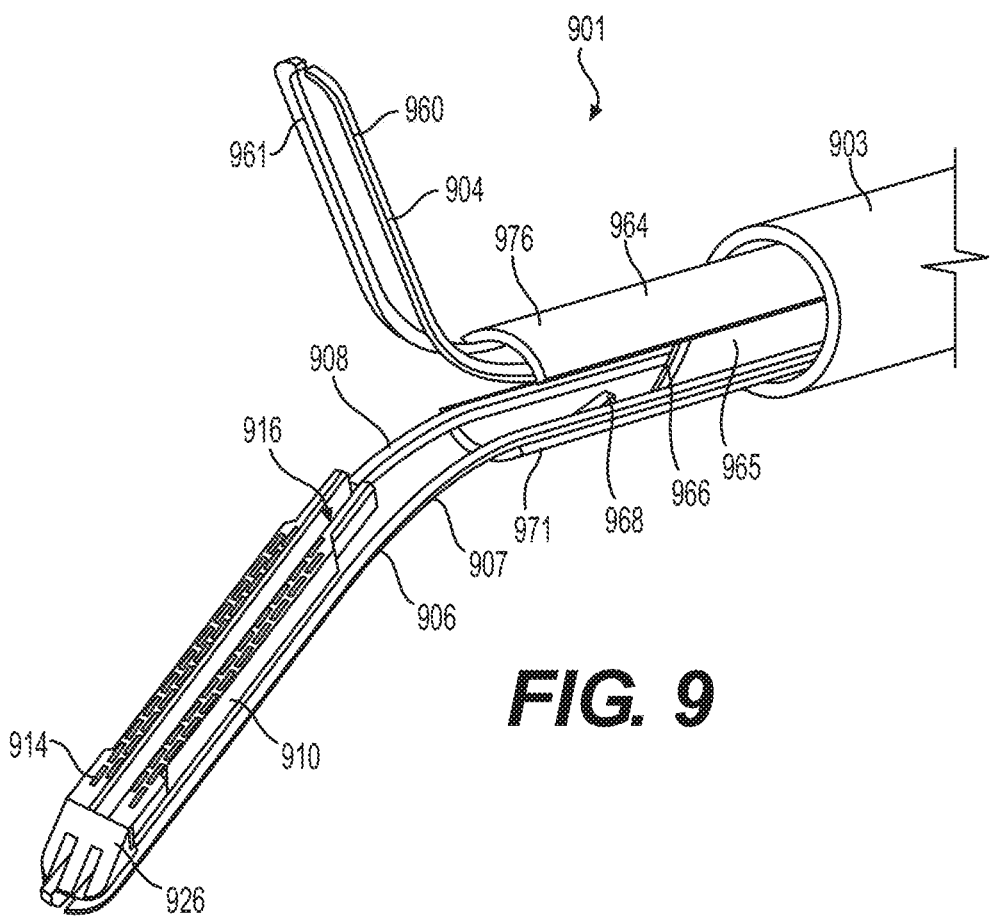
FIG. 9 is a perspective view of an exemplary surgical stapler system, according to aspects of this disclosure.

FIG. 9 shows another embodiment of a stapling apparatus 901 including an anvil 904 and distal bodies 906, 907 positioned within a flexible catheter 903. Apparatus 901 may have any of the features previously described in relation to the other apparatuses of this disclosure. Apparatus 901 may include an I-beam 964 partially surrounding at least proximal portions of anvil 904 and distal bodies 906, 907. Anvil 904 and distal bodies 906, 907 may be curved and biased to an open position (shown in FIG. 9) in the same manner as distal bodies 106, 107 and anvil 104. Anvil 904 may include a first anvil body 960 and a second anvil body 961 that substantially align with distal bodies 906, 907, respectively. Proximal portions of each of first anvil body 960, second anvil body 961, and distal bodies 906, 907 may be positioned between top portion 970 and bottom portion 971 of I-beam 964. I-beam 964 may be positioned within a lumen of flexible catheter 903 or a working channel of an endoscope or other medical device. I-beam 964 may be coupled to a flexible wire (not shown) at a proximal portion of I-beam 964. The flexible wire may extend proximally to a handle/actuator that may be activated by a user to move I-beam 964 proximally and distally relative to anvil 904 and distal bodies 906, 907. Cartridge 910 may be coupled to distal bodies 906, 907 via a protrusion (not shown) fit between distal bodies 106, 107 forming a snap-fit coupling, one or more hooks, or other coupling mechanisms including those described in other embodiments herein. In some examples, cartridge 910 may be coupled to distal bodies 906, 907 via protrusions extending from cartridge 910 received within grooves of distal bodies 906, 907, in substantially the same manner that grooves 130, 132 may slidably receive protrusions or tangs 131, 133 of stapler cartridge 110 (as shown in FIG. 5).

I-beam 964 may include a top portion 970, a bottom portion 971, an intermediate portion 965 connecting the top portion 970 to the bottom portion 971, and two ramp actuators 968, 969. Top portion 970 and bottom portion 971 may be curved and may be configured to move within a working channel of a medical device or a lumen of flexible catheter 903. In some examples, top portion 970 and bottom portion 971 may have substantially the same length and width relative to their longitudinal axes, may have substantially the same radius of curvature, and/or otherwise may be mirror images of one another. Intermediate portion 965 may be flat, with planar surfaces and a distal edge 966. Distal edge 966 may be sharp and may be configured to cut tissue. Intermediate portion 965 may extend longitudinally substantially parallel with the longitudinal axes of top portion 964 and bottom portion 971, and longitudinal ends of edge 966 may be coupled to radially-inner surfaces of top portion 964 and bottom portion 971. In some examples, I-beam 964 may include two ramp actuators 968, 969 configured to deploy fasteners from cartridge 910. Ramp actuators 968, 969 may extend radially inward from a radially-inner surface of bottom portion 971 (shown in FIG. 10) or top portion 970. Each ramp actuator 968, 969 may include a radially-inward facing surface that extends proximally from a radially-inward facing surface of bottom portion 971. Ramp actuators 968, 969 may be configured to align with channels of cartridge 910. I-beam 964 may be configured to move via movement of the aforementioned wire coupled to a proximal portion of I-beam 964.

Figures 10, 11:
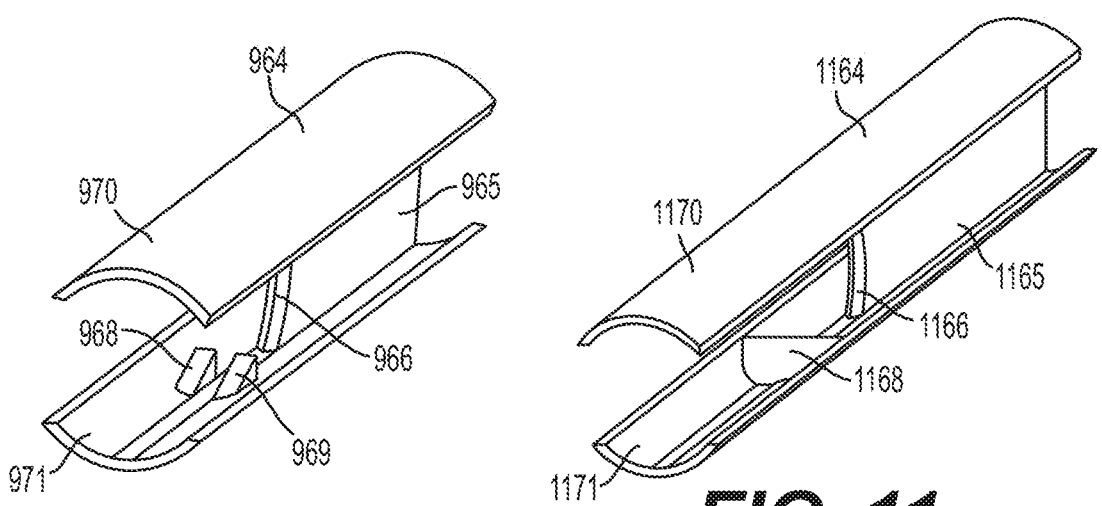
FIG. 10 is a perspective view of an exemplary component of a surgical stapler system, according to aspects of this disclosure.
FIG. 11 is a perspective view of an exemplary component of a surgical stapler system, according to aspects of this disclosure.

FIG. 11 shows an alternative embodiment of an I-beam 1164 with top portion 1170, bottom portion 1171, intermediate portion 1165, edge 1166, and a single ramp actuator 1168. I-beam 1164 may have any of the characteristics previously described in relation to I-beam 964. A single ramp actuator 1168 may extend distally from a radially-inward facing surface of bottom portion 1171 and may include a curved distal end.

Cartridge 910 may include any of the features previously described in relation to cartridges 110, 610, 710, 810. Cartridge 910 may include openings 914 configured to deploy fasteners and a longitudinal slot 916 configured to receive a cutting device, such as edge 966 of I-beam 964. A distal portion 926 of cartridge 910 may be angled relative to the longitudinal axis of cartridge 910. In addition, cartridge 910 may include one or more cavities configured to receive one or more actuation ramps 968, 971, 1168. Cartridge 910 may be configured to align with distal bodies 906, 907. In some examples, anvil 904 and/or distal bodies 906, 907 may extend to the proximal end of apparatus 901. In some examples, the proximal ends of distal bodies 906, 907 may be coupled to control wires, and the control wires may be configured to be pulled proximally from the proximal end to move anvil 904 and distal bodies 906, 907 to a closed position.

A user may use apparatus 901 to couple one or more fasteners to tissue by first positioning tissue between anvil 904 and distal bodies 906, 907. In some examples, a user may first backload I-beam 964 including a wire coupled to a proximal portion of I-beam 964, anvil 904, and distal bodies 906, 907 through the distal end of a working channel of an endoscope, and move the wire and proximal portions of anvil 904 and distal bodies 906, 907 out of a proximal end of the endoscope prior to inserting apparatus 901 into a patient's body. Then, in some examples, the user may grasp tissue using a grasper or other tool to move tissue between anvil 904 and distal bodies 906, 907. Once tissue is positioned in the active region of apparatus 901, a user may translate a wire coupled to I-beam 964 distally and cause I-beam 964 to push anvil 904 and distal bodies 906, 907 radially-inward due to the interface between top portion 970 and bottom portion 971 on the one hand and anvil 904 and distal bodies 906, 907 on the other hand. Moving I-beam 964 distally may cause anvil 904 and distal bodies 906, 907 to close or clamp down onto tissue. As I-beam 964 is pushed distally towards tissue, edge 966 may engage and cut tissue. When cartridge 910 is positioned between top portion 970 and bottom portion 971, actuation ramps 968, 969 may move into a cavity of cartridge 910 and contact one or more pistons, similar to pistons or spaces 751 shown in FIG. 7. As a user moves I-beam 964 distally, actuation ramps 968, 969 may deploy fasteners from openings 914 by moving pistons within cartridge 910. As the user continues to move I-beam distally, edge 966 and intermediate portion 965 may be positioned within channel 916. Since anvil 904 and distal bodies 906, 907 are biased radially outward, anvil and distal bodies 906, 907 may be slidably engaged with I-beam 964 to hold anvil 904 and distal bodies 906, 907 in a closed, clamped position while fasteners are deployed from cartridge 910.

Each of the aforementioned apparatuses and devices may be used to grasp, couple, and/or cut tissue. In some examples, a user may load a proximal portion of a stapler device in a working channel of an endoscope by backfeeding the proximal portion through a distal end of an endoscope working channel to position a portion of the elongate body within the working channel. Once the proximal portion is positioned within a working channel, a handle assembly with one or more actuation devices may be coupled to the proximal end of the apparatus. The user may then introduce the endoscope into the patient's body and move the endoscope towards a target area. The user may locate a target area (such as a tumor or other diseased tissue) present in a body lumen of a subject using the endoscope by directly visualizing the target area using an image sensor. Once the user has positioned the endoscope's distal end proximate to a target area, the user may position a tissue acquisition tool within a working channel of the endoscope, if such a tool is not already present. When the distal end of the endoscope is positioned at the target area, the user may then position tissue between or close to the active portion of the apparatus, e.g. the space between the apparatus's anvil and distal bodies. Once tissue is positioned within the stapler device's active portion, the user may move the stapler device's anvil and distal bodies to a closed position and clamp down on the grasped tissue with the apparatus. The user may then actuate an actuator to deploy fasteners into the clamped tissue and against the stapler device's anvil. In some examples, the user may actuate a knife in the apparatus to cut portions of the target tissue either before, during, or after fastening tissue together via fasteners.

By providing a stapler instrument that a user may replace an empty staple cartridge with a stapling cartridge full of fasteners without having to remove the stapler instrument from a patient's body during a procedure, a user may reduce overall procedure time and avoid unnecessary harm to a patient's body caused by the repeated removal and re-insertion of a stapler instrument when replacing an empty stapling cartridge.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A fastening device comprising:
 a flexible longitudinal body including a central longitudinal axis and a distal end;

an anvil extending distally from the distal end of longitudinal body; and a distal body extending distally from the distal end of the longitudinal body, the distal body configured to removably receive a cartridge having a plurality of fasteners, wherein the distal body includes a first distal body and a second distal body separated by a gap configured to receive the cartridge;

wherein at least one of the anvil and the distal body is flexible and has a first configuration with a distal portion of the at least one of the anvil and the distal body extending radially outward from the central longitudinal axis and a second configuration with the distal portion closer to the central longitudinal axis than in the first configuration.

2. The device of claim 1, wherein the fastening device includes a protrusion extending from a surface of anvil, wherein the protrusion is configured to engage the distal body.

3. The device of claim 1, wherein the at least one of the anvil and the distal body is the anvil; and
wherein the distal body is flexible and has a first configuration with a distal portion of the distal body extending radially outward from the central longitudinal axis and a second configuration with the distal portion of the distal body closer to the central longitudinal axis than in the first configuration.

4. The device of claim 3, wherein each of the distal body and the anvil is curved in the respective first configuration and substantially straight in the second configuration.

5. The device of claim 4, wherein the cartridge includes an actuation wire extending proximally from a proximal end of the cartridge through a channel of the longitudinal body; and wherein the actuation wire is configured to move proximally relative to the cartridge and the anvil to deploy fasteners from the cartridge.

6. The device of claim 4, wherein the distal body includes a first distal body and a second distal body spaced from the first distal body, wherein the cartridge includes a distal protrusion extending distally from a distal surface of the cartridge, and wherein the distal protrusion is configured to be received between distal ends of the first distal body and the second distal body.

7. The device of claim 1, further comprising the cartridge removably coupled to the distal body.

8. The device of claim 7, wherein the distal body includes a groove configured to slidably receive a flange of the cartridge.

9. The device of claim 7, wherein a distal portion of the cartridge includes a locking portion configured to be received by a locking gap of the distal body.

10. The device of claim 1, further comprising a flexible catheter configured to translate relative to the longitudinal body, wherein the flexible catheter moves one or more of the anvil and the distal body towards each other when the flexible catheter is moved distally relative to the longitudinal body.

11. The device of claim 1, further comprising:
an I-beam including a top portion, a bottom portion, a distal-facing sharp edge and at least one actuation ramp, and
the cartridge, wherein the cartridge is configured to receive the at least one actuation ramp,
wherein the I-beam moves proximally and distally relative to the anvil and the distal body.

12. The device of claim 11, wherein the distal-facing sharp edge is proximal to a distal end of the I-beam and extends between the top portion and the bottom portion.

13. The device of claim 1, further comprising a cartridge configured to hold a plurality of fasteners and including a proximal elongate extending proximally from a proximal end of the cartridge, wherein the proximal elongate includes a lumen and at least one actuation wire positioned within the lumen, and wherein the actuation wire is configured to deploy fasteners from the cartridge and/or actuate a knife within the cartridge.

14. The device of claim 1, wherein each of the distal body and the anvil includes a radially-inward facing surface having at least one of a roughened surface, serrations, and teeth.

15. A tissue fastening device comprising:
a flexible tube;
a fastener device positioned within a lumen of the flexible tube, the fastener device comprising:
a flexible anvil that has a first configuration with a distal portion of the anvil extending radially outward from a central longitudinal axis of the fastener device and a second configuration with the distal portion of the anvil closer to the central longitudinal axis of the fastener device than in the first configuration, wherein the anvil includes a protrusion extending from a surface of the anvil;
a flexible distal body configured to removably receive a cartridge of fasteners, wherein the flexible distal body has a first configuration with a distal portion of the flexible distal body extending radially outward from the central longitudinal axis of the fastener device and a second configuration with the distal portion closer to the central longitudinal axis of the fastener device than in the first configuration, wherein the protrusion is configured to engage the flexible distal body;
wherein the tube is configured to translate distally relative to the fastener device to transition each of the anvil and the flexible distal body from the respective first configuration to the respective second configuration.

16. The device of claim 15, further comprising the cartridge removably coupled to the flexible distal body.

* * * * *